United States Patent [19]

Johlin, Jr.

[11] Patent Number: 5,383,849
[45] Date of Patent: Jan. 24, 1995

[54] METHOD FOR SELECTIVE ENDOSCOPIC CANNULATION OF DUCTAL STRUCTURES

[75] Inventor: Frederick C. Johlin, Jr., Iowa City, Iowa

[73] Assignee: Wilson-Cook Medical, Inc., Winston-Salem, N.C.

[21] Appl. No.: 881,215

[22] Filed: May 11, 1992

[51] Int. Cl.⁶ .............................................. A61M 31/00
[52] U.S. Cl. ........................................ 604/53; 604/95
[58] Field of Search ............................ 604/49, 53–54, 604/95, 280, 281; 128/4, 4 SM

[56] References Cited

U.S. PATENT DOCUMENTS

| | | | |
|---|---|---|---|
| 4,577,637 | 3/1986 | Mueller, Jr. | 128/658 |
| 4,592,341 | 6/1986 | Omagari et al. | 128/4 |
| 4,799,474 | 1/1989 | Ueda | 128/4 |
| 4,934,340 | 6/1990 | Ebling et al. | 128/6 |
| 5,024,617 | 6/1991 | Karpiel | |
| 5,055,101 | 10/1991 | McCoy | 604/95 |
| 5,109,830 | 5/1992 | Cho | 128/4 |

Primary Examiner—C. Fred Rosenbaum
Assistant Examiner—Corrine Maglione
Attorney, Agent, or Firm—Woodard, Emhardt, Naughton, Moriarty & McNett

[57] ABSTRACT

A method and device for selective endoscopic cannulation is disclosed. The cannulator includes an elongated intermediate portion which is normally straight and flexible and a distal tip portion which flexibly deviates in a specific direction away therefrom. The cannulator also includes a referential coupling, maintained in fixed relation within the cannulator, which allows bending of the cannulator along a portion of the length of the cannulator in a first plane which is transverse to the longitudinal axis of the referential coupling while resisting bending in other transverse planes relative thereto. The cannulator is advanceable through the operating channel of an endoscope and through the entrance into the ductal system, where it can be positioned with the referential coupling located at the entrance to the ductal system. When so located, the referential coupling maintains a predictable orientation between the cannulator and the ductal entrance in dependence upon the position of the operating end of the endoscope relative to the ductal entrance. By manipulating the endoscope and cannulator relative the ductal entrance, with the referential coupling maintaining the predicted relative orientation between the cannulator and the entrance in response to these manipulations, the tip of the cannulator can thus be predictably maneuvered within the ductal system to thereby locate and cannulate the desired ductal structure therein.

8 Claims, 5 Drawing Sheets

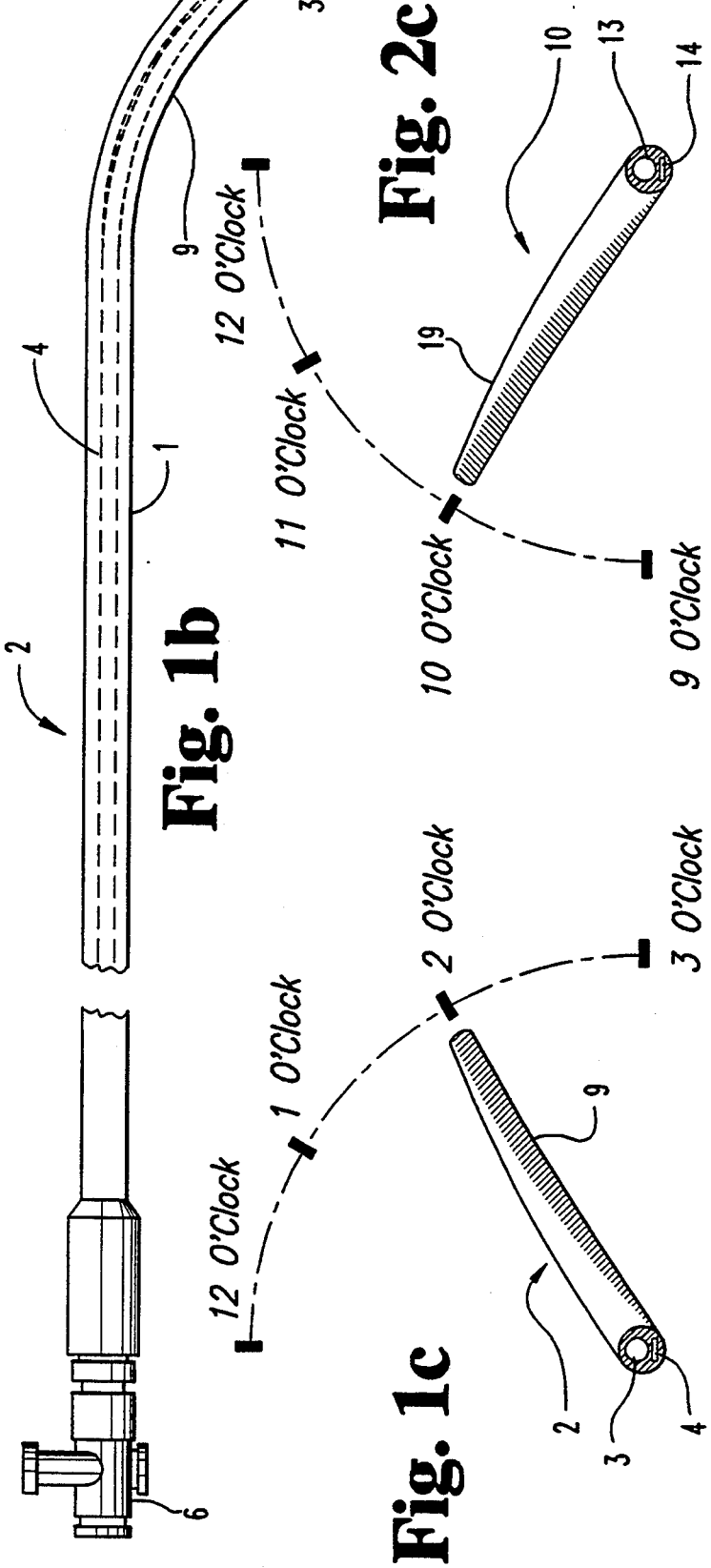

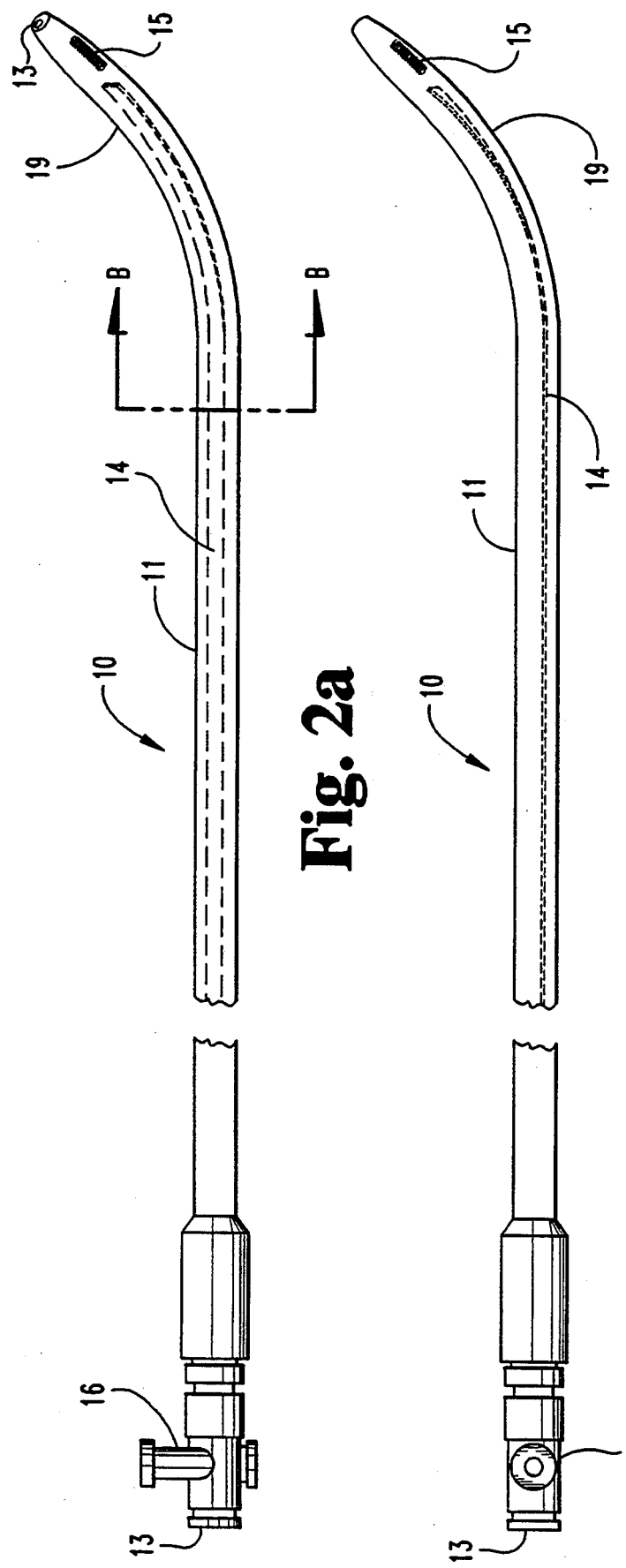

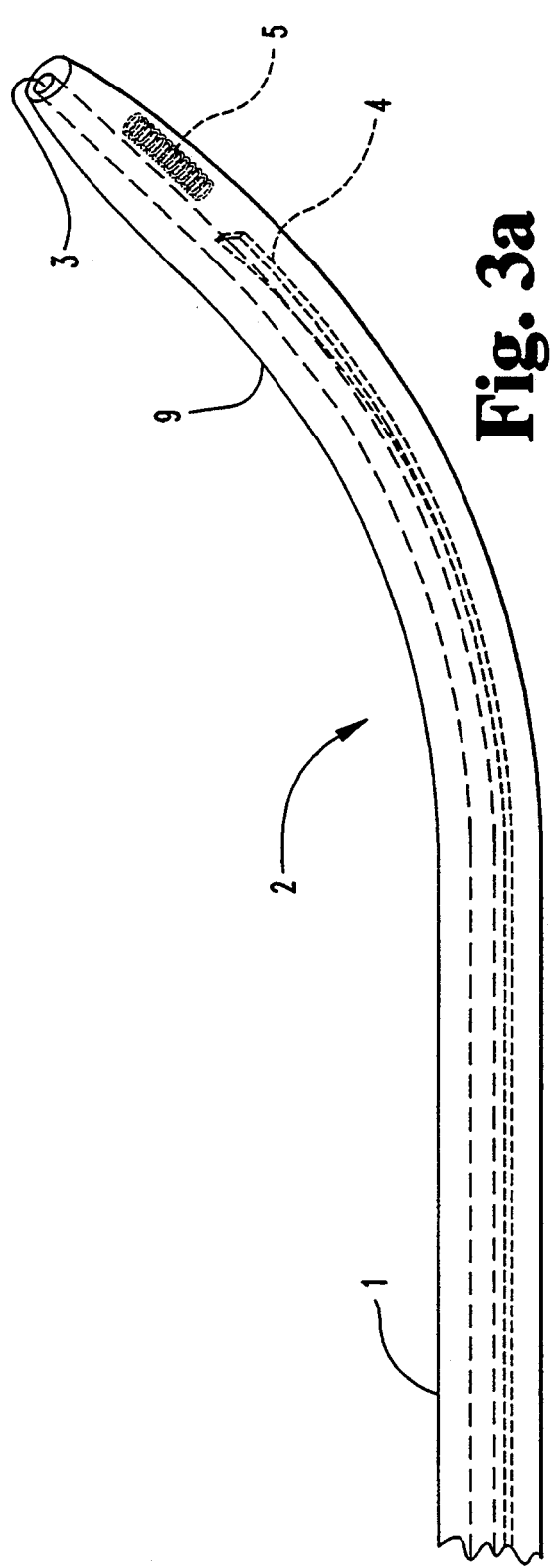
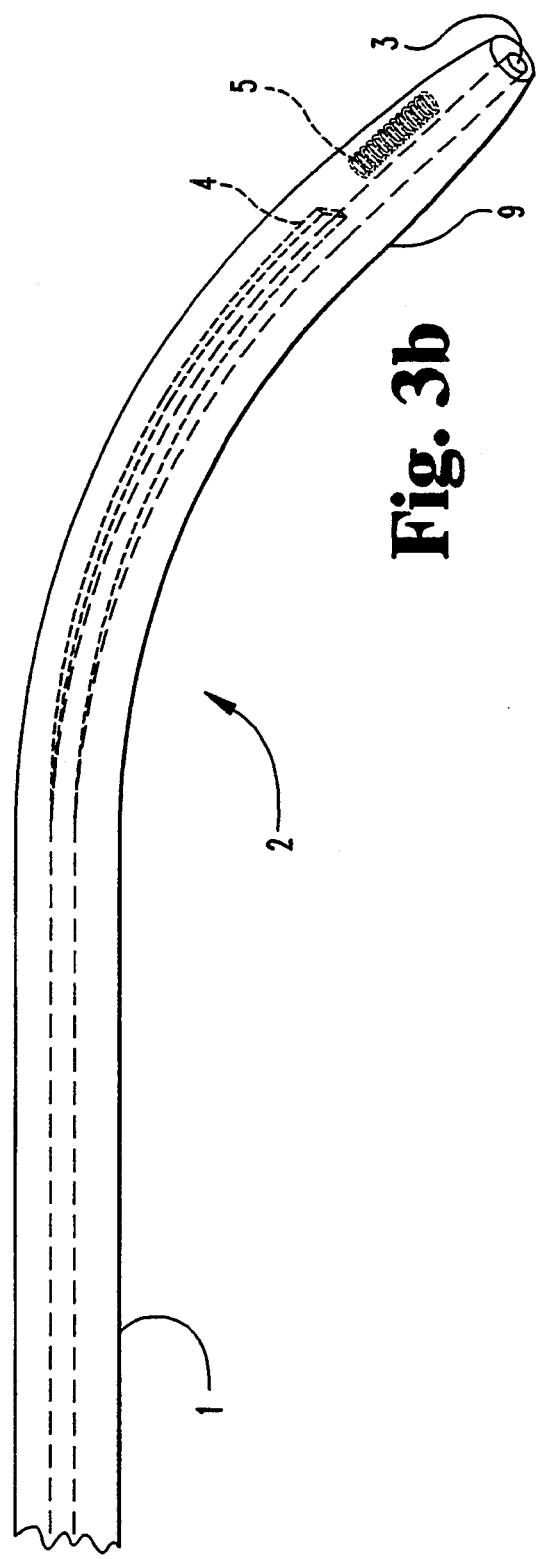

METHOD FOR SELECTIVE ENDOSCOPIC CANNULATION OF DUCTAL STRUCTURES

BACKGROUND OF THE INVENTION

Cannulae used in endoscopic retrograde cholangiopancreatography (ERCP) allow access to the bile or pancreatic ducts through the sphincter of Oddi which opens into the duodenum at the papilla of Vater. When performing an ERCP procedure, difficulty is sometimes encountered in the attempt to successfully cannulate the desired duct within this ductal system. This difficulty can result in a prolongation of the procedure or possibly inadequate diagnosis and/or therapy, which can possibly cause severe and sometimes life-threatening consequences.

Previous devices designed to facilitate selective access of the segments within the biliary tree have included steerable catheters, bowed papillotomes, and curved tip wire guides. None of these devices have satisfactorily provided precise control of the cannula tip and therefore have proven inadequate for selective cannulation. Fully steerable cannulas have not enjoyed wide acceptance because they are too bulky for practical operation through the biopsy channel of a pancreaticobiliary endoscope. Thinner steerable devices, which are capable of steering in only one or two directions, offer little advantages over a standard catheter.

Bowed papillotomes are sometimes used like a standard catheter to gain access to specific structures within the biliary ductal system. When used in this manner, however, the cutting wire of the bowed papillotome interferes with the cannulation process, while the only advantage over a standard catheter that is provided is additional flexion for redirecting the tip in only one direction. As a result, bowed papillotomes are awkward to use and fail to provide improved effectiveness.

Commonly used to gain access to many structures within the body, wire guides are also commonly used to effect cannulation of ducts within the biliary ductal system. Guide wires, however, carry the risk of blunt trauma to structured segments of the bile or pancreatic ducts which can result in life-threatening infection, perforation or pancreatitis. Given the present alternatives, there is a need and usefulness for a new approach which extends the utility of endoscopic cannulas that are used to secure selective intraluminal access to hollow tubular structures, such as are found in the pancreaticobiliary tree.

SUMMARY OF THE INVENTION

The present invention provides for precisely directed endoscopic cannulation for the purpose of selective access within the pancreaticobiliary ductal system. In addition to providing precise directional control for selectively accessing specific segments of the pancreaticobiliary tree, the present invention may be useful to gain cannulation within other ductal systems as well.

The method of cannulation described and claimed involves introducing a specially constructed selective cannulator through an endoscope and into a patient. The selective endoscopic cannulator defines a cannulating lumen and includes an elongated intermediate portion, which is normally straight and flexible and which defines a longitudinal axis, and a distal tip portion which flexibly deviates in a specific direction away from the longitudinal axis defined by said intermediate portion. The cannulator also includes a referential coupling, maintained in fixed relation within the cannulator, which allows bending of the cannulator along a portion of the length of the cannulator in a first plane which is transverse to the longitudinal axis of the referential coupling while resisting bending in other transverse planes relative thereto.

The cannulator is advanced through the operating channel of the endoscope and through the entrance into the ductal system, where it is positioned such that the referential coupling is located at the entrance to the ductal system, wherein the referential coupling, by allowing bending in a specific transverse plane relative thereto at the ductal entrance while resisting bending in other transverse planes, maintains a predictable orientation between the cannulator and the ductal entrance in dependence upon the position of the operating end of the endoscope relative to the ductal entrance. By manipulating the endoscope and cannulator relative the ductal entrance, with the referential coupling maintaining the predicted relative orientation between the cannulator and the entrance in response to these manipulations, the tip of the cannulator can thus be predictably maneuvered within the ductal system to thereby locate and cannulate the desired ductal structure.

A specially constructed cannulator device for selectively cannulating ductal structures within a ductal system for use with the method of the present invention is also described and claimed herein. In the illustrated embodiment, the selective endoscopic cannulator includes a multi-lumen tubular catheter, and has an elongated intermediate portion which is normally straight and flexible and which defines a longitudinal axis, and a distal tip portion which flexibly deviates in a specific direction away from the longitudinal axis defined by said intermediate portion. One inner lumen, which provides cannulated access to the distal tip of the cannulator, is circular in cross-section and is sized to receive a wire guide therein with sufficient spacing to allow contrast medium to be injected therethrough with the wire guide positioned within the lumen. The second inner lumen is rectangular in cross-section and contains a flat wire of nickel titanium alloy, which acts as a referential coupling by maintaining a predictable relative orientation between the cannulator and the entrance to the ductal system in dependence upon the relative direction of angled entry of the cannulator into the ductal system. The proximal and distal end of the rectangular lumen are sealed. Implanted in the rectangular lumen at the distal tip of the cannula is a platinum coil which is highly visible on fluoroscopy.

In one illustrated embodiment of the selective cannulator of the present invention. The distal tip portion is oriented in a 2 o'clock position relative to the longitudinal axis of the intermediate straight portion of the cannulator. So configured, the cannulator has been found to be particularly suited for cannulation of the left hepatic duct and segments of the pancreatic duct. In a second illustrated embodiment, the distal tip portion is oriented in a 10 o'clock position relative to the longitudinal axis of the intermediate straight portion of the cannulator. This 10 o'clock configuration is particularly suited for cannulating the cystic duct and gall bladder, and the right hepatic duct.

According to one important aspect of the present invention, there is provided a selective cannulator with a referential coupling that maintains a predictable orientation between the cannulator with respect to the entrance to a ductal system in dependence upon the relative direction of angled entry whereby, as the cannulator is manipulated within the ductal system, a predictable orientation is maintained for the tip of the cannula within the ductal system being probed. By this means, precise directional cannulation of almost any ductal structure can be simply accomplished.

This invention extends the utility of endoscopic cannulas which are used to secure selective intraluminal access to hollow tubular structures, such as are found in the pancreaticobiliary tree, and can be used to gain selective access to structures within other ductal systems as well. Within the pancreaticobiliary tree alone, the present invention facilitates selective cannulation of: 1) the cystic duct and gallbladder; 2) the left hepatic duct and the intrahepatic ducts thereafter; 3) the right hepatic duct and the intrahepatic ducts thereafter; 4) segments within the pancreatic duct; or 5) abscesses or pseudocysts contained in the pancreas and pancreatic duct.

BRIEF DESCRIPTION OF THE DRAWINGS

FIGS. 1 a—c are views of a "2 o'clock" cannulator for selective endoscopic cannulation according to the present invention. FIG. 1 a is a segmented side elevational view of the cannulator, showing the location of the flat wire referential coupling of nitinol material within the cannulator in dashed lines, and also showing platinum coil in the distal tip of the cannulator. FIG. 1b is a top plan view of the "2 o'clock" cannulator of FIG. 1a. FIG. 1c is a sectioned view of the "2 o'clock" cannulator of FIGS. 1 a—b, sectioned along lines A—A in FIG. 1 a, and illustrating the relative 2 o'clock orientation of the distal tip of the cannulator.

FIGS. 2a—c are views of a "10 o'clock" cannulator for selective endoscopic cannulation according to the present invention. FIG. 2a is a segmented top plan view of the cannulator, showing the location of the flat wire referential coupling of nitinol material within the cannulator in dashed lines, and also showing platinum coil in the distal tip of the cannulator. FIG. 2b is a side elevational view of the "10 o'clock" cannulator of FIG. 2a. FIG. 2c is a sectioned view of the "10 o3 clock" cannulator of FIGS. 2a—b, sectioned along lines B—B in FIG. 2a, and illustrating the relative 10 o'clock orientation of the distal tip of the cannulator.

FIGS. 3a–b are enlarged views, respectively, of the tip portion of the "2 o'clock" cannulator shown in FIGS. 1 a—b. FIGS. 3a—b illustrate the relative orientation of the cannulating lumen, nitinol flat wire, and platinum coil within the cannulator.

DESCRIPTION OF THE PREFERRED EMBODIMENT

Figure 4A:
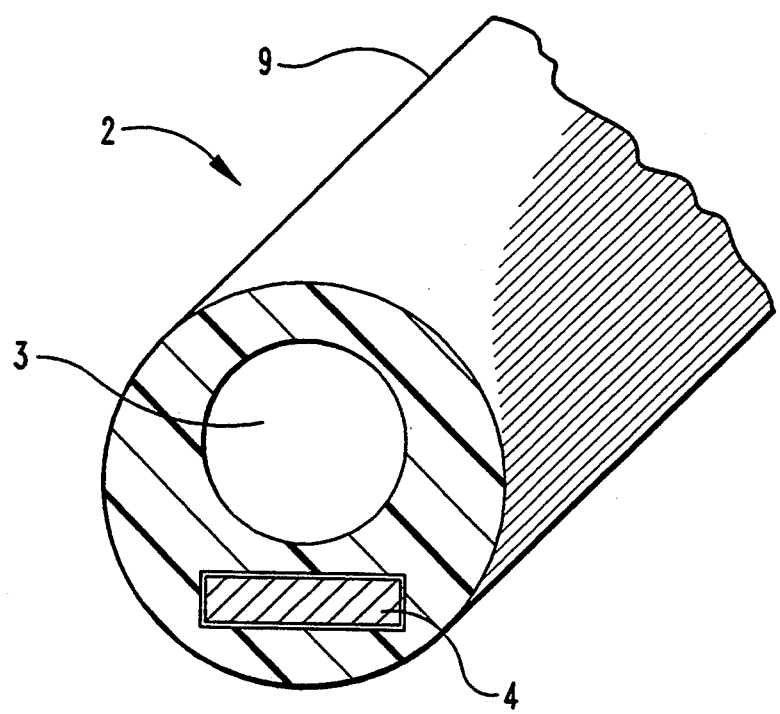
FIGS. 4a is a further enlarged cross-sectional view of the cannulator of FIGS. 1 a–b, cross-sectioned along lines A—A.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now to the drawings, FIGS. 1 a–c are views of a "2 o'clock" cannulator 2 for selective endoscopic cannulation according to the present invention. FIG. 1 a is a segmented side elevational view of cannulator 2, showing the location of a flat wire 4 of nitinol material within cannulator 2. Owing to its superelastic properties and its reliably reproducible flexion, nitinol is considered to be particularly suited for use in flat wire 4. Spring steel may adequately serve as an alternative material, particularly for devices which are designed for one time use. FIG. 1 a also shows platinum coil 5 in the distal tip portion 9 of cannulator 2. Platinum is known to be an exceptionally radio-dense metal, and thereby provides for precise fluoroscopic localization of cannulator 2 within the body during the cannulation procedure.

Cannulator 2 has an intermediate portion 1 which is straight and flexible and which therefore normally defines a longitudinal axis, and a distal end portion 9 which is molded to flexibly deviate therefrom in a 2 o'clock direction relative thereto (where 12 o'clock is the normally medial direction relative to an endoscope as cannulator 2 exits therefrom, which orientation is reliably repeatable each time cannulator 2 is advanced through an endoscope owing to the bending of flat wire 4 at the curvature portion of the operating channel at the operating end of the endoscope). The shaft cannulator 2 is made of extruded transluscent Teflon material which has been heat molded into the deviating curvature at distal tip portion 9, as shown. At its distal end, cannulator 2 is tapered to a reduced diameter as well to facilitate insertion into and dilation of smaller ductal structures. Also shown in FIG. 1a, at the proximal end of cannulator 2, is a standard Luer-Lock adapter 6 which provides access into cannulator 2 for the wire guide insertion, injection of contrast medium, and aspiration.

FIG. 1b is a top plan view of the "2 o'clock" cannulator of FIG. 1 a. FIG. 1c is a sectioned view of the 2 o'clock cannulator of FIGS. 1 a–b, sectioned along lines A—A in FIG. 1a, and illustrates the relative 2 o'clock orientation of the distal tip portion 9 of cannulator 2, and shows a first cannulating lumen 3, which is circular in cross-section, and flat wire 4, which is maintained in fixed relation within cannulator 2 inside a second, rectangularly shaped lumen.

Similarly, FIGS. 2a–c are views of a "10 o'clock" cannulator 10 for selective endoscopic cannulation according to the present invention. FIG. 2a is a segmented top plan view of cannulator 10, showing the location of flat wire 14 of nitinol material within cannulator 10, and also showing platinum coil 15 located within the distal tip portion 19 of cannulator 10. Intermediate portion 11 is straight and flexible and normally defines a longitudinal axis, from which distal end portion 19 is molded to flexibly deviate in a 10 o'clock direction relative thereto. Also shown in FIG. 2a, at the proximal end of cannulator 2, is a standard Luer-Lock adapter 16.

FIG. 2b is a side elevational view of the "10 o'clock" cannulator of FIG. 2a. FIG. 2c is a sectioned view of the "10 o'clock" cannulator of FIGS. 2a–b, sectioned along lines B—B in FIG. 2a, and illustrating the relative 10 o'clock orientation of the distal tip 19 of cannulator 10, and the internal orientation of cannulating lumen 13 and flat wire 14 within cannulator 10.

FIGS. 3a–b are enlarged views, respectively, of the distal end of intermediate portion 1 and the distal tip portion 9 of the "2 o'clock" cannulator 2 shown in FIGS. 1 a–b. FIGS. 3a–b illustrate the relative orientation of cannulating lumen 3, nitinol flat wire 4, and platinum coil 5 within cannulator 2. In FIGS. 3a–b, it is seen that flat wire 4 extends within distal tip portion 9. Maintained within its constricting rectangular lumen within cannulator 2, flat wire 4 is twisted to conform to the deviating curvature of distal tip portion 9. In this relative configuration, with flat wire 4 extending within distal tip portion 9, the directional flexion of distal tip portion is further assured relative to the longitudinal axis of intermediate portion 1. Alternatively, flat wire 4 may be positioned to only extend within intermediate portion 1. In this relative configuration, the directional flexion of distal tip portion 9 is due solely to the molded shape of the Teflon (or other suitable) material which forms the shaft of the distal tip portion 9. Also, flat wire 4 may be sized to extend only along only a portion of the distal end of intermediate portion 1 of cannulator 2, or may be constructed to extend the entire length thereof. A suitable length is in the range of 30–60 cm. at the distal end which is adequate for positioning within both the curvature in the operating channel of the endoscope and the ductal entrance. Longer lengths, while not adding to overall operability, may adequately function for the purpose intended.

Figure 4B:
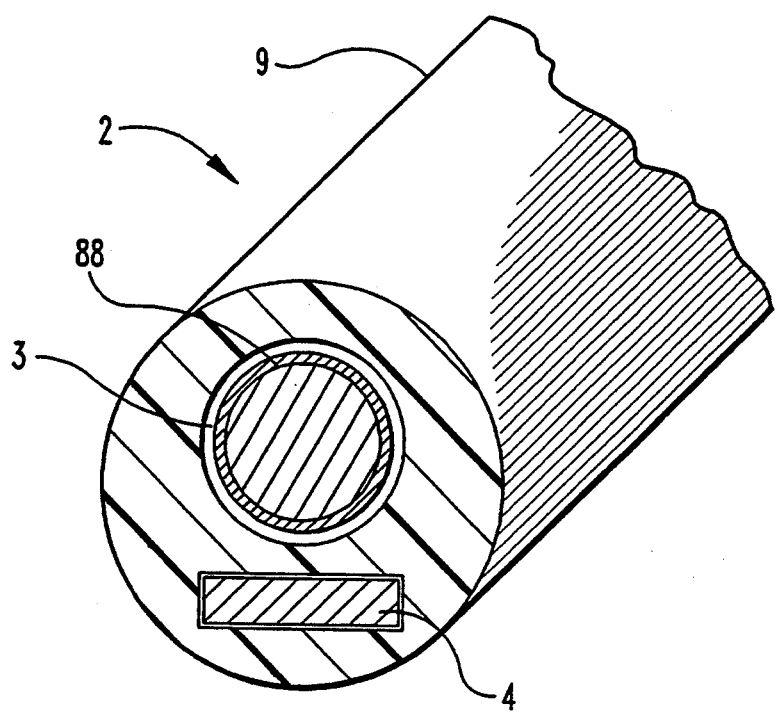
FIG. 4b is an illustration of the cross-sectional view of FIG. 4a with a wire guide positioned within the cannulating lumen of the cannulator.

FIGS. 4a is a further enlarged cross-sectional view of cannulator 2 of FIGS. 1 a–b, cross-sectioned along lines A—A. FIG. 4b is an illustration of the cross-sectional view of FIG. 4a with wire guide 88 positioned within cannulating lumen 3 of cannulator 2, with sufficient spacing to allow contrast medium to be injected therethrough while wire guide 88 is so positioned.

An illustrative example of the method of selective cannulation of the present invention utilizing the above described instrumentation will now be described. First, an endoscope is introduced into the patient and positioned with its operating end in proximity with the Sphincter of Oddi. A wire guide is then advanced through the operating channel of the endoscope and through the ductal entrance to gain access into the ductal system. A selective endoscopic cannulator, as described above, is then advanced over the wire guide, through the operating channel of the endoscope, and through the entrance into the ductal system.

The cannulator is then positioned with its referential coupling (flat wire) located at the Sphincter of Oddi, so that, by allowing bending in a specific transverse plane relative thereto at the Sphincter of Oddi while resisting bending in other transverse planes, the referential coupling maintains a predictable orientation between the cannulator and the ductal entrance in dependence upon the position of the operating end of the endoscope relative to the ductal entrance. By manipulating the endoscope and cannulator relative the ductal entrance with the referential coupling located at the entrance thereto to predictably maneuver the tip of the cannulator within the ductal system, the desired ductal structure can thereby be easily located and cannulated.

Figure 5C:
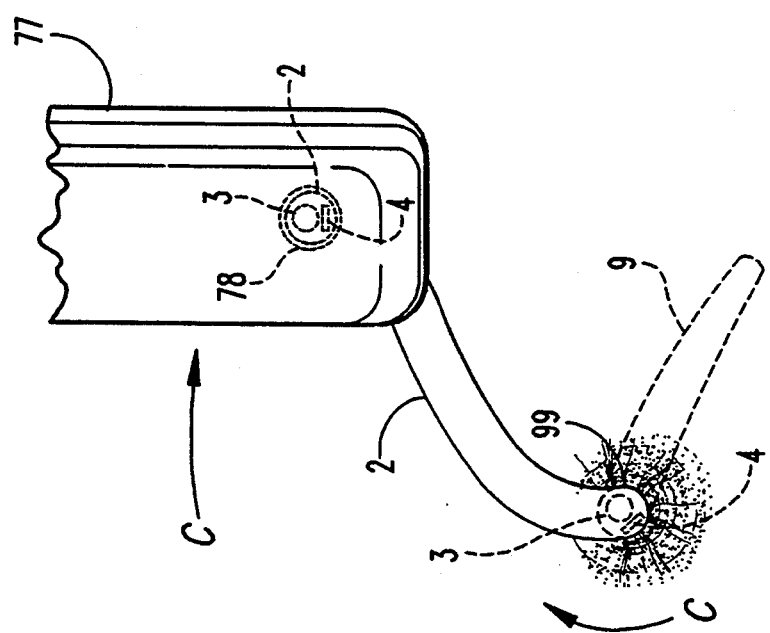
FIGS. 5a–c illustrate the technique for manipulating the tip of a selective cannulator of the present invention within a ductal system by maneuvering the endoscope about the entrance to the ductal system while the flat wire of nitinol material acts as a referential coupling thereat.
Figure 5B:
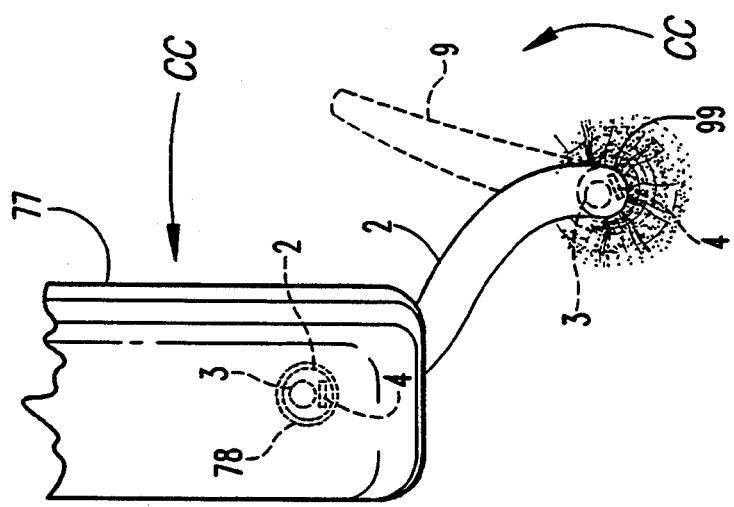
Figure 5A:
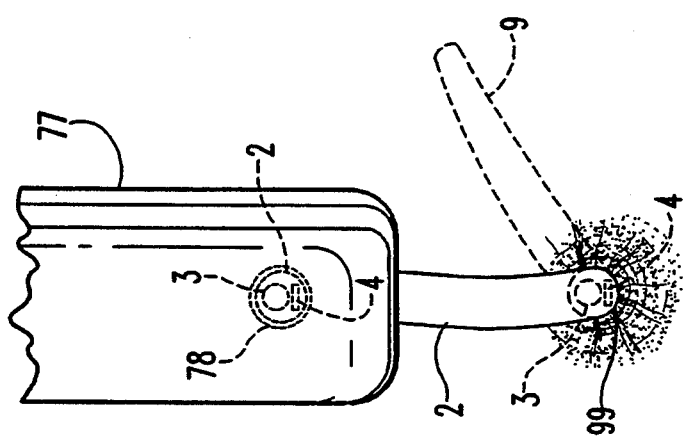

FIGS. 5a–c illustrate the above described technique for manipulating the tip of a selective cannulator 2 of the present invention within a ductal system by maneuvering endoscope 77 about the entrance 99 (Sphincter of Oddi) to the ductal system (pancreatobiliary tree) while flat wire 4 acts as a referential coupling between cannulator 2 and entrance 99. In FIG. 5a, 2 o'clock cannulator 2 is shown advanced through the operating channel 78 of endoscope 77 and through the Sphincter of Oddi 99 into the biliary duct, with referential coupling 4 positioned within both the Sphincter of Oddi 99 and the curvature of the operating channel 78 at the end of endoscope 77. In this position, and with endoscope 77 in a 12 o'clock orientation with respect to the Sphincter of Oddi 99, the distal end portion 9 of cannulator 2 assumes its natural 2 o'clock orientation.

FIGS. 5b–c illustrate the precise maneuverability of cannulator 2 within the pancreatobiliary tree that is obtainable by manipulating endoscope 77 about the Sphincter of Oddi 99. In FIG. 5b, endoscope 77 has been moved in a counterclockwise direction CC about ductal entrance 99, and the relative corresponding counterclockwise movement of the distal tip portion 9 of cannulator 2 within the ductal system is shown, owing to the referential coupling effect between cannulator 2 and ductal entrance 99 that has been formed by flat wire 4. In this figure, it is seen that, by allowing bending in only one direction, flat wire 4 causes distal tip portion 9 of cannulator 2 to rotate relative to ductal entrance 99 as endoscope 77 is moved thereabout.

In FIG. 5c, the effect of the opposite movement, in a clockwise direction C, of endoscope 77 about ductal entrance 99, and the relative corresponding clockwise movement of distal tip portion 9 of cannulator 2 within a ductal system is shown. Owing to the referential coupling effect between of flat wire 4 and ductal entrance 99, referential coupling 4 causes distal tip portion 9 of cannulator 2 to correspondingly rotate relative to ductal entrance 99 in a clockwise direction in response to the clockwise movement of endoscope 77 about ductal entrance 99.

It is to be noted that FIGS. 5a–c show referential coupling 4 positioned within both the curvature of the operational channel 78 of endoscope 77 and ductal entrance 99 during the manipulation procedure. By so maintaining a referential coupling between cannulator 2 and both endoscope 77 and ductal entrance 99, a higher degree of precision in the relative movement of cannulator 2 may be obtained at the sacrifice of an overall loss of a degree of freedom of movement.

By appropriately selecting a selective cannulator of the present invention with the desired orientation of its distal tip portion, any of a wide variety of ductal structures can be easily and simply cannulated. For example, the 2 o'clock cannulator, as above described, is particularly suited for cannulation of the left hepatic duct and segments of the pancreatic duct. The orientation of the second illustrated embodiment, the 10 o'clock cannulator, is particularly suited for cannulating the cystic duct and gall bladder, and the right hepatic duct.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A method for selective endoscopic cannulation of a desired ductal structure within a ductal system of a patient, said method comprising the steps of:

introducing an endoscope into the patient, said endoscope defining an operation channel providing remote operative access into the body of the patient, and positioning the operating end of the endoscope in proximity with an entrance into the ductal system;

advancing a selective endoscopic cannulator through the operating channel of the endoscope and through the entrance into the ductal system, the cannulator including an elongated intermediate portion which is normally straight and flexible and which defines a longitudinal axis, and a normally curved distal tip portion which extends distally from said intermediate portion and normally flexibly deviates in a specific direction away from the longitudinal axis defined by said intermediate portion and generally toward the desired ductal structure when endoscopically positioned within the ductal system, the cannulator further including referential coupling means, maintained in fixed relation within the cannulator, for allowing bending of the cannulator along a portion of the length of the cannulator in a first plane which is transverse to the longitudinal axis of said referential coupling means while resisting bending in other transverse planes relative thereto;

positioning the cannulator such that the referential coupling means is positioned at the entrance to the ductal system, wherein the referential coupling means, by allowing bending in a specific transverse plane relative thereto at the ductal entrance while resisting bending in other transverse planes, maintains a predictable orientation between the cannulator and the ductal entrance in dependence upon the position of the operating end of the endoscope relative to the ductal entrance; and manipulating the cannulator within the ductal system to locate and cannulate the desired ductal structure, wherein said manipulating step includes the step of rotating the operating end of the endoscope about the ductal entrance with the referential coupling means positioned thereat, by which the referential coupling means causes the tip of the cannulator to correspondingly rotate within the ductal system to thereby locate the desired ductal structure for cannulation.

2. The method for selective endoscopic cannulation of a desired ductal structure within a ductal system of a patient of claim 1 in which the endoscope has a curvature in its operating channel, and in which said method additionally comprises the step of positioning said referential coupling at both the ductal entrance and the curvature of the operating channel at the end of endoscope.

3. The method for selective endoscopic cannulation of a desired ductal structure within a ductal system of a patient of claim 1 in which the distal tip portion of the cannulator normally deviates in a 2 o'clock direction relative to the normal longitudinal axis of the intermediate portion.

4. The method for selective endoscopic cannulation of a desired ductal structure within a ductal system of a patient of claim 3 in which the ductal structure being cannulated is the left hepatic duct.

5. The method for selective endoscopic cannulation of a desired ductal structure within a ductal system of a patient of claim 3 in which the ductal structure being cannulated is the pancreatic duct.

6. The method for selective endoscopic cannulation of a desired ductal structure within a ductal system of a patient of claim 1 in which the distal tip portion of the cannulator normally deviates in a 10 o'clock direction relative to the normal longitudinal axis of the intermediate portion.

7. The method for selective endoscopic cannulation of a desired ductal structure within a ductal system of a patient of claim 6 in which the ductal structure being cannulated is the cystic duct.

8. The method for selective endoscopic cannulation of a desired ductal structure within a ductal system of a patient of claim 6 in which the ductal structure being cannulated is the right hepatic duct.

* * * * *